(12) United States Patent
Hunziker et al.

(10) Patent No.: US 6,583,399 B1
(45) Date of Patent: Jun. 24, 2003

(54) OPTICAL RESONATOR MICROSPHERE SENSOR WITH ALTERING Q-FACTOR

(75) Inventors: Guido Hunziker, Altadena, CA (US); Paul M. Bridger, Pasadena, CA (US); Ming Cai, Pasadena, CA (US); Kerry J. Vahala, San Gabriel, CA (US)

(73) Assignee: California Institute of Technology, Pasadena, CA (US)

( * ) Notice: Subject to any disclaimer, the term of this patent is extended or adjusted under 35 U.S.C. 154(b) by 24 days.

(21) Appl. No.: 09/721,463

(22) Filed: Nov. 22, 2000

Related U.S. Application Data
(60) Provisional application No. 60/166,957, filed on Nov. 22, 1999.

(51) Int. Cl.[7] .............................................. H01J 40/14
(52) U.S. Cl. ................................................. 250/214 R
(58) Field of Search ................................ 250/573, 576, 250/227.11, 227.14, 214 R; 356/436, 440, 441, 442

(56) References Cited

U.S. PATENT DOCUMENTS

| | | | |
|---|---|---|---|
| 4,071,753 A | 1/1978 | Fulenwider et al. | 250/227 |
| 4,345,482 A | 8/1982 | Adolfsson et al. | 73/862.59 |
| 4,419,895 A | 12/1983 | Fuller | 73/517 |
| 4,592,043 A * | 5/1986 | Williams | 359/126 |
| 4,678,905 A | 7/1987 | Phillips | 250/227 |
| 4,839,527 A * | 6/1989 | Leitch | 250/227.23 |
| 4,979,959 A | 12/1990 | Guire | 623/66 |
| 5,143,854 A | 9/1992 | Pirrung et al. | 436/518 |
| 5,910,661 A * | 6/1999 | Colvin, Jr. | 250/227.14 |
| 6,023,540 A * | 2/2000 | Walt et al. | 345/808 |
| 6,266,459 B1 * | 7/2001 | Walt et al. | 345/808 |

OTHER PUBLICATIONS

Khoobehi et al., "Fluorescent Microsphere Imaging: A Particle–Tracking Approach to the Hemodynamic Assessment of the Retina and Choroid", Opthalmic Surgery and Lasers, vol. 28(11), Nov. 1997.*

Schafer, Dorothy A., Gelles, Jeff, Sheetz, Michael P., & Landick, Robert; *Transcription by single molecules of RNA polymerase observed by light microscopy*; Nature, vol. 352; Aug. 1, 1991; pp. 444–448.

Yin, Hong, Wang, Michelle D., Svoboday, Karel, Landick, Robert, Block, Steven M. & Gelles, Jeff; *Transcription Against an Applied Force*; Science, vol. 270; Dec. 8, 1995; pp. 1653–1657.

(List continued on next page.)

*Primary Examiner*—David Porta
*Assistant Examiner*—Stephen Yam
(74) *Attorney, Agent, or Firm*—Christie, Parker & Hale, LLP

(57) ABSTRACT

An optically based resonating sensor useful for detecting and discriminating specified substances present in the environment is provided. The resonating sensor comprises a light source and a coupler adapted to allow light to pass from the light source to a resonator wherein the light is stored for a specified period of time. The resonator is coupled to the coupler such that some portion of the light passing through the coupler enters the resonator and some portion of the light resonating within the resonator exits the resonator to the coupler. The outer surface of the resonator is modified such that the interaction of the modified outer surface of the resonator with a specified substance in the environment alters some characteristic of the light flowing through the sensor system. A detector is arranged to observe and detect the interactions between the modified outer surface and the light flowing through the system.

20 Claims, 7 Drawing Sheets

OTHER PUBLICATIONS

Cai, Ming and Vahala, Kerry; *Highly Efficient optical power transfer to whispering–gallery modes by use of a symmetrical dual–coupling configuration*; Optics Letters, vol. 25, No. 4; Feb. 15, 2000; pp. 260–262.

Anderson, George P.; Golden; Joel P. & Ligler, Frances, S; *A fiber optic biosensor: combination tapered fibers designed for improved signal acquisition*; Biosensors & Bioelectronics, vol. 8; 1993; pp. 249–256.

Treussart, F.; Hare, J. Collot, L.; Lefevre, V.; Weiss, D.S.; Sandoghdar, V.; Raimond, J.M. & Haroche, S; *Quantized atom–field force at the surface of a microsphere*; Optics Letters; vol. 19, No. 20; Oct. 15, 1994; pp. 1651–1653.

Cai, et al., Fiber–Optic Add–Drop Device Based on a Silica Microsphere–Whispering Gallery Mode System, IEEE Photonics Technology Letters, Jun. 1999, pp. 686–687, vol. 11, No. 6, IEEE.

Gorodetsky, et al., High–Qoptical whispering–gallery microresonators: precession approach for spherical mode analysis and emission patterns with prism couplers, Optics Communications 113, Dec. 15, 1994, pp. 133–143, vol. 113, Elsevier Science B.V.

Gorodetsky, et al., Ultimate Q of optical microsphere resonators, Optics Letters, Apr. 1, 1996, pp. 453–455, vol. 21, No. 7, Optical Society of America.

Griffel, et al., Morphology–dependent resonances of a microsphere–optical fiber system, Optics Letters, May 15, 1996, pp. 695–697, vol. 21, No., 10, Optical Society of America.

Ilchenko, et al., Pigtailing the high–Q microsphere cavity: a simple fiber coupler for optical whispering–gallery modes, Optics Letters, Jun. 1, 1999, pp. 723–725, vol. 24, No. 11, Optical Society of America.

Knight, et al., Phase–matched excitation of a whispering–gallery–mode resonances by a fiber taper, Optics Letters, Aug. 1, 1997, pp. 1129–1131, vol. 22, No. 15, Optical Society of America.

Sandoghdar, et al., Very low threshold whispering–gallery–mode microsphere laser, Physical Review A, Sep. 1996, pp. R1777–R1780, vol. 54, No. 3, The American Physical Society.

Schafer, et al., Transcription by single molecules of RNA polymerase observed by light microscopy, Letters to Nature, Aug. 1, 1991, pp. 444–448, vol. 352.

Serpengüzel, et al., Excitation of resonances of microspheres on an optical fiber, Optics Letters, Apr. 1, 1995, pp. 654–656, vol. 20, No. 7, Optical Society of America.

Yin, et al., Transcription Against an Applied Force, Science, Dec. 8, 1995, pp. 1653–1657, vol. 270.

\* cited by examiner

OPTICAL RESONATOR MICROSPHERE SENSOR WITH ALTERING Q-FACTOR

CROSS-REFERENCE TO RELATED APPLICATION

This application is based on U.S. application Ser. No. 60/166,957, filed Nov. 22, 1999, the disclosure of which is incorporated by reference.

STATEMENT REGARDING FEDERALLY SPONSORED RESEARCH

The U.S. Government has certain rights in this invention pursuant to grant awarded by the Federal Government.

FIELD OF THE INVENTION

The present invention is directed to an optical resonator sensor for detecting the presence of specific chemical and/or biological species.

BACKGROUND OF THE INVENTION

This invention relates in general to optical resonating sensors and in particular to optical resonating sensors for detecting and discriminating the presence of specific biological, chemical, etc. substances comprising a resonator specifically modified to interact with the substance by converting the interaction between the resonator and the substance into modulated light signals.

Sensors designed to take advantage of the mechanical, electrical or optical resonating properties of a material are well-known in the art. One type of conventional optical resonating sensor employs fiberoptic techniques. Various mechanical means couple the end of the output optical fiber to a mechanical or acoustic source. The mechanical or acoustic signal from the source varies the optical coupling coefficient between the two fibers so that by measuring such coefficient, the mechanical or acoustic information can be measured. For example, in U.S. Pat. No. 4,071,753 to Fulenwider et al., the ends of an input and an output optical fiber are aligned and light is transmitted from one fiber to the other, while Fuller, U.S. Pat. No. 4,419,895 discloses a sensor comprising a pair of optical fibers which are parallel but somewhat misaligned. In the above-described type of transducers, the optical sensor comprises two optical fibers optically coupled. The optical coupling coefficient between the two fibers varies with the physical parameter to be measured, so that by measuring such coefficient, the parameter can be detected and measured.

In another type of optical sensor the physical parameter to be measured modulates the vibrational motion of a transducer. Such modulation changes the intensity of light coupled between the ends of two optical fibers so that by measuring such changes the physical parameter can be detected and measured. The transducer element may be a vibrating spring, a ferroelectric or a piezoelectric element such as a quartz crystal. Such transducers are disclosed in U.S. Pat. No. 4,345,482 to Adolfsson et al.

In yet another type of optical sensor, a physical parameter moves a piezoelectrical member coupled to a fiberoptic in a direction transverse to the light transmitted in an fiberoptic so that the modulations of the movement also modulate the light transmitted by the member. In some embodiments the physical parameter causes relative motion between two flexible light transmitting members. The change in the amount of light transmitted between the two members is detected and analyzed to determine the physical parameter of interest. Such sensors are disclosed in U.S. Pat. No. 4,678,905 to Phillips.

In all the above-described applications for optical sensors, a non-optical, often mechanical, detector provides signals which alter the characteristics of light passing through a fiberoptic. These changes in the transmission of light are then processed by electronic circuitry. Such detectors are ultimately only as sensitive as the mechanical construct and further are often subject to electromagnetic interference which is undesirable.

Optical sensors have been developed to replace these traditional mechanical/electrical sensors to measure physical variables not possible with electrical sensors and to provide better performance. Other reasons for preferring optical over electrical signal sensing and transmission is the elimination of electromagnetic interference and inherent electrical isolation. One example of such an optical sensor disclosed by Anserson, et al., is a fiberoptic biosensor-combination using evanescently coupled fiber tapers. Anserson, et al., BIOSENSORS AND BIOELECTRONICS, vol. 8, pg. 249–256, (1993). However, these sensors still have a detection resolution that is limited by the perturbations induced at the surface of the fiberoptic itself.

The whispering-gallery-mode (WGM) was discovered by Lord Rayleigh over 100 years ago in the field of acoustics. The most obvious manifestation of the whispering-gallery-mode occurs in a building which has a vaulted gallery architecture. In these buildings a sound as faint as a whisper is transmitted via a whispering-gallery-mode along the vault and is readily propagated over a long distance without loss of energy.

This type of propagation has also found application in other fields including microwave and optical techniques. The property has recently been explored in dielectric microsphere resonators owing to their ultrahigh optical quality factors or Q-factors. The Q factor is a measure of the stability of light stored within a resonator, in affect the number of periods or cycles of time before the light energy decays to a critical level, which in turn effects the sensitivity of the resonator to external perturbations. For example, typical mechanical or electrical resonators such as quartz crystals have Q-factors ranging from 100 to 1,000. In comparison, the Q factors found for some silica microsphere resonators can be as high as 8 billion, indicating that the microsphere are capable of storing light energy for as many as 8 billion light cycles, resulting in a significant increase in resonator sensitivity. Gorodetsky, et al., OPTICS LETTERS, vol. 21, pg. 453, (1996). In addition, there have been significant advances in coupling these high Q-factor resonators to sources of optical power. A recent publication reported that certain optical-fiber-taper to silica-microsphere whispering-gallery-resonator systems show critical, or ideal coupling, yielding coupling efficiencies as high as 99.8%. Knight, et al., OPTICS LETTERS, vol. 22, pg. 1129 (1997); and Cai, et al., IEEE PHOTON. TECHNOL. LETT., vol. 11, No. 6, pg. 686, (1999).

These systems have several advantages over those previously utilized, including that no sophisticated optical coupling is required as input and output light is always guided and manipulated in optical fiber, the system can attain Q's in excess of 1 million even when the microsphere is in contact with the taper, thereby eliminating in certain cases the need for sophisticated sub-micron piezo actuators, and the system is inherently robust owing to its all-fiberoptic construction.

Despite the promise shown by these optical-fiber-taper to silica-microsphere whispering-gallery-resonator systems and their acknowledged potential to open up a range of new applications, no work has been done to explore their potential as sensors. Accordingly, as a need exists for ever more sensitive optical sensor systems to detect and discriminate the presence of substances in the environment, it is important to explore these optical-fiber-taper to silica-microsphere whispering-gallery-resonator systems potential as sensors.

SUMMARY OF THE INVENTION

The present invention is directed to a system and method for utilizing an optical resonator system to sensitively detect substances of interest. This invention utilizes a surface modified resonator coupled to a light propagating coupler to provide high sensitivity substance specific detection systems. This invention is also directed to novel methods for detecting a wide range of substances using the resonating sensor of the invention.

In one embodiment, the invention is directed to a resonating sensor comprising a source of light, a detector, a coupler for receiving and conducting light from the light source and a resonator having an outer surface. The resonator is optically coupled to the coupler to allow a portion of the light passing through the coupler to enter the resonator and to be stored within the resonator for a specified period of time, and a portion of the light resonating within the resonator to exit the resonator. The outer surface of the resonator is modified such that when a substance of interest comes into contact with the modifier, it binds with the modifier, altering the complex susceptibility of the modifier such that the interaction between the modifier and the light resonating within the resonator is detectably altered. The detector is arranged such that the interaction between the modifier and the light resonating within the resonator can be monitored and recorded.

In a preferred embodiment, the resonator is evanescently coupled to the coupler and light is resonating inside the resonator in whisper-gallery modes. In this embodiment, the resonator is preferably a silica microsphere and the coupler is preferably a dual-taper fiber waveguide.

In another preferred embodiment, the modifier is a biological or chemical modifier adapted to alter the complex susceptibility of the surface of the resonator when a specific substance interacts with the modifier such that as the substance interacts with the modifier a mode loss is induced in the resonator, decreasing the transmission of light through the resonator. In this embodiment, the detector is adapted to detect the transmission spectrum of light passing through the system such that as transmission of light through the resonator decreases the signal associated with such loss is recorded.

In yet another preferred embodiment the resonating sensor system of the present invention comprises an array of couplers, each coupler linked to an independent resonators which has been modified to interact with a unique substance. In this embodiment the couplers are arrayed on a substrate and each are in optical communication with a source of light having a unique wavelength and a detector such that all resonators can be monitored simultaneously.

In still yet another embodiment, the invention is directed to a system for the detection of substances comprising a source of light in optical communication with a series of resonating sensors as described above.

In still yet another additional embodiment, the invention is directed to a method for detecting and discriminating a substance in contact with the resonating sensor. The method comprises analyzing the air in an environment using a resonating sensor as described above.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
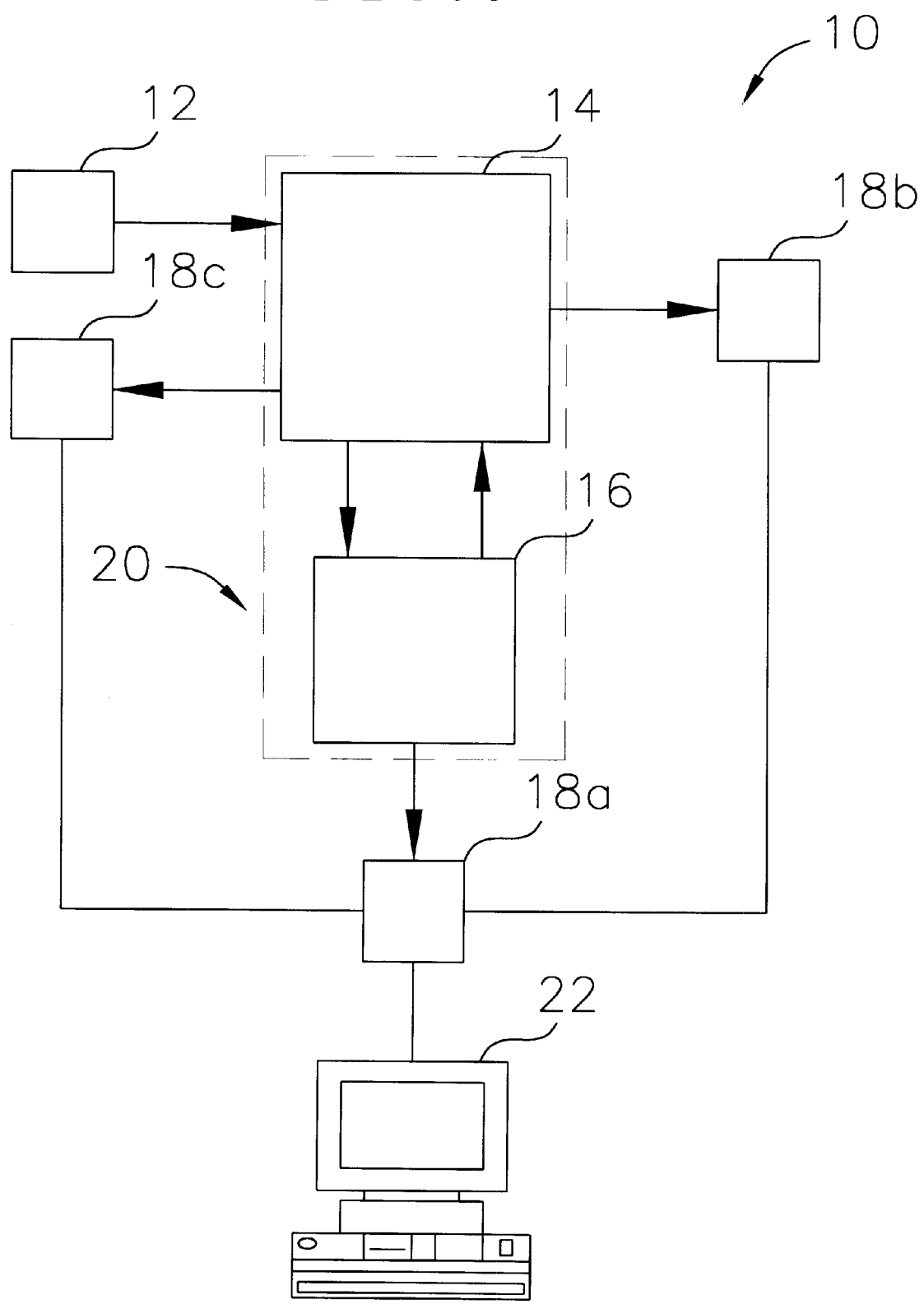
FIG. 1 is a schematic view of an embodiment of the resonating sensor according to the invention.

The present invention is directed to an optical resonating sensor for detecting and discriminating substances in contact with the sensor. In one embodiment, as shown in FIG. 1, the resonating sensor 10 comprises a source of light 12, a coupler 14 adapted to receive light from the source of light 12, a resonator 16 optically coupled to the coupler, and at least one detector 18a, 18b, and 18c adapted to observe light exiting some portion of the resonating sensor.

Light is introduced into the coupler 14 from the source of light 12 such that the light is conducted through the coupler 14. The resonator 16 is placed in proximate relation to the coupler 14 such that a portion of the light passing through the coupler 14 is coupled into the resonator 16 and a portion of the light passes out of the coupler 14. A portion of the light coupled into the resonator 16 resonates within the resonator 16 in one or more resonant modes for a period of time determined by the Q-factor of the resonator 16, a portion of the light exits the resonator 16 to the environment, and a portion of the light is coupled back into the coupler 14 and passes out of the coupler 14. A detector or series of detectors 18a, 18b, and 18c, are adapted to observe the light exiting the coupler/resonator pair 20. The detector(s). 18a, 18b, and 18c can be arranged such that light exiting the resonator 16 to the environment enters the detector 18a, or the detector can be arranged to detect the light transmitted through 18b or reflected from 18c the coupler 14. The signal produced by the light entering the detector(s) 18a, 18b, and 18c is output to a suitable monitor 22. Any device having the ability to detect changes in amplitude, frequency, phase or wavelength of the transmitted light can be used as a detector and monitor 22, such as, for example a turnable photomultiplier in signal communication with a computer. Additionally, any suitable source of light 12 may be used in the subject invention, such as, for example, a turnable wavelength laser or a broad spectrum lamp so long as detectable levels of light are transmitted to the detector.

In general terms, the coupler/resonator pair 20 comprises a resonator 16 in coupling communication with a coupler 14 which is in optical communication with a light source 12. The coupler 14 and the resonator 16 are constructed such that the light passing through the coupler 14 evanescently couples into the resonator 16 to create a reservoir of stored light resonating within the resonator 16. The coupler 14 can comprise any construct suitable for coupling light from a light source 12 into an optical resonator 16, such as, for example, a prism or a waveguide.

In one preferred embodiment a waveguide coupler 14 having proximal and distal ends is utilized. The proximal end of the waveguide coupler 14 is placed in optical communication with the light source 12 and the distal end is placed in optical communication with the detector 18a, 18b, and 18c. A resonator 16 is evanescently coupled at any point along the length of the waveguide coupler 14 such that light from the light source 12 enters the waveguide coupler 14 at its proximal end and moves there along to the resonator 16 coupled thereto and then to the detector(s) 18a, 18b, and 18c arranged at the distal end of the waveguide coupler 14. In this embodiment the waveguide 14 may have any cross-section suitable for evanescent coupling with the resonator, such as, for example, a tapered fiber waveguide, a ridge waveguide, a slab waveguide, a D-fiber waveguide, a cylindrical taper waveguide, or an elliptical taper waveguide. Preferably, the waveguide has a diameter in the range of 1 to 5 microns, and more preferably 3 to 5 microns. Waveguides can be prepared from standard telecommunication fiber by any standard technique. D-fiber waveguides, for example, may be prepared by etching a standard waveguide with any suitable acid, such as, hydroflouric acid. Techniques for preparing fiber tapers have been disclosed, for example, in Cai et al., IEEE PHOTON. TECHNOL. LETT., vol. 11, pg. 686 (1999); and Knight et al., OPT. LETT., vol. 22, pg. 1129, (1997), which are incorporated herein by reference.

To couple the light entering the coupler 14 to the resonator 16 the resonator 16 and coupler 14 must be positioned relative to one another such that the evanescent field (or decaying field external to the coupler 14) created by the light passing through the coupler 14 couples to the resonator 16. In the embodiment shown in the attached figures, the resonator 16 and the coupler 14 are in physical contact, however, any suitable spacing can be used such that the light in the coupler 14 and the resonator 16 are evanescently coupled. For example, a piezo-manipulator can be used to position the resonator 16 proximate to, but not in contact with the coupler 14 such that evanescent coupling occurs.

The optical resonator 16 can comprise any suitable resonator design, such as, for example, microspheres or rings, such that light entering the resonator 16 from the coupler 14 resonates within the resonator in at least one resonant mode for a specified period of time. In one preferred embodiment the resonator 16 is a microsphere resonator and the light resonates within the resonator 16 in the whispering-gallery modes of the microsphere resonator. Preferably the microsphere resonator has a diameter of less than 1 mm, more preferably the microsphere resonator has a diameter in the range of 50 to 150 microns, and more preferably about 100 microns. Such microsphere resonators 16 can be fabricated utilizing any known technique, for example, microspheres of the preferred size can be fabricated by first preparing a sharp-tipped filament of fiber using a laser and then reheating the tip to achieve the desired sized sphere. Although a material such as silica is preferably used for the resonator 16 due to the high-Q factors of the material and the ease with which it can be shaped into appropriate microspheres, the resonators 16 can also be made of any suitable material, such as, for example, glass, doped glass or plastic (e.g., polystyrene).

Figure 2A:
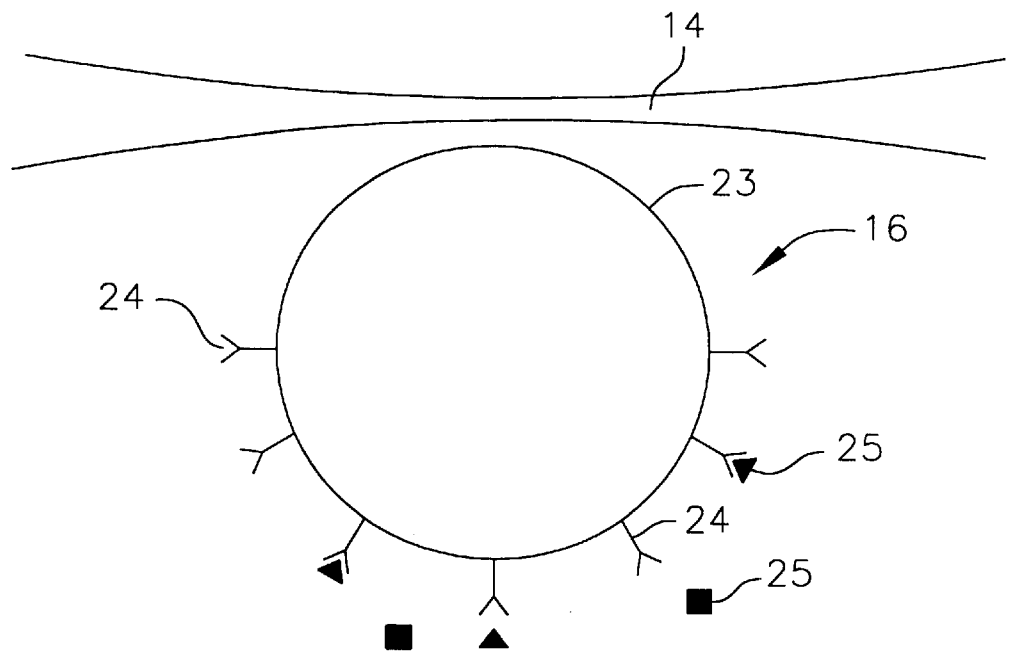
FIG. 2a is a schematic view of an alternative embodiment of the coupler/resonator scheme according to the invention.
Figure 2B:
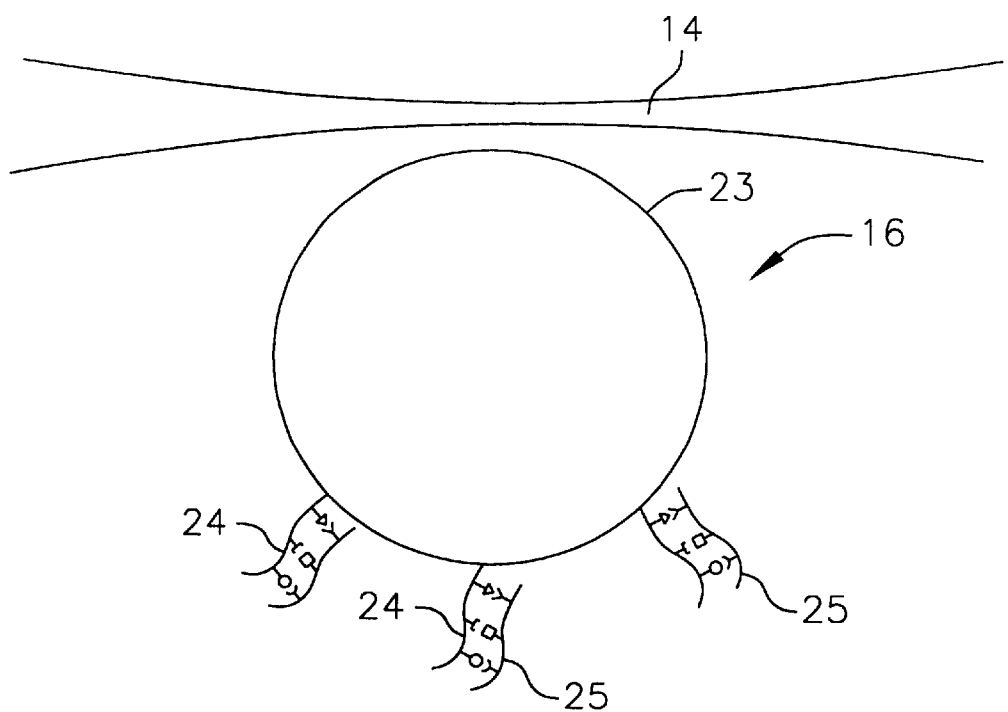
FIG. 2b is a schematic view of an alternative embodiment of the coupler/resonator scheme according to the invention.
Figure 2C:
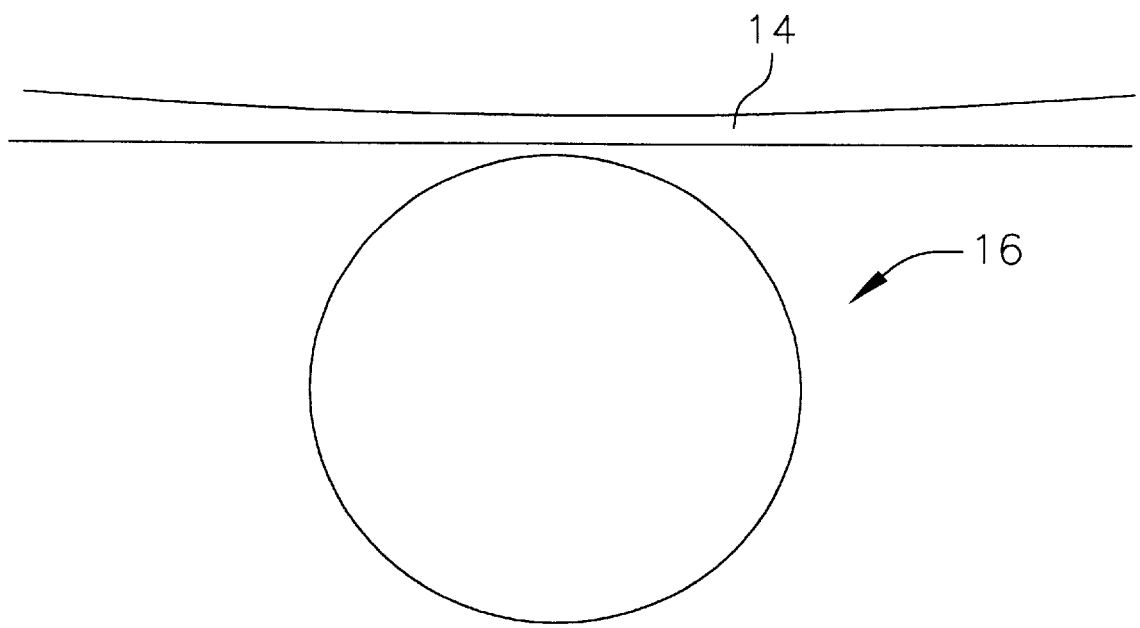
FIG. 2c is a schematic view of an alternative embodiment of the coupler/resonator scheme according to the invention.
Figure 2D:
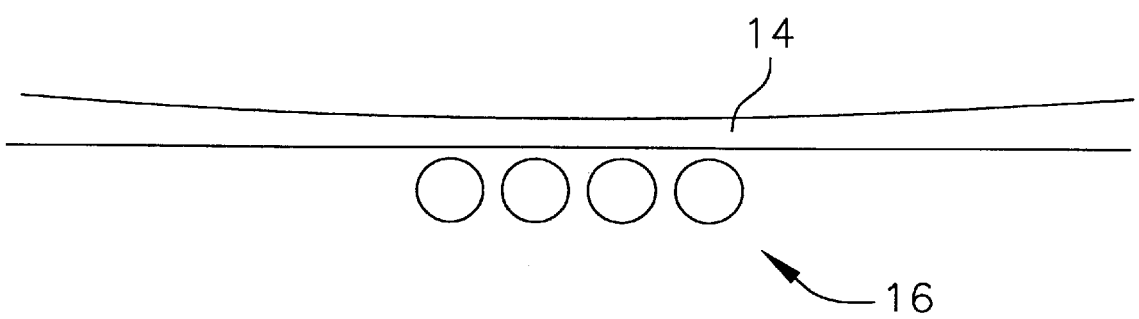
FIG. 2d is a schematic view of an alternative embodiment of the coupler/resonator scheme according to the invention.

The outer surface 23 of the optical resonator 16 is modified with a modifier 24. FIGS. 2a and 2b show the coupler/resonator pair 20 of FIG. 1 in further detail, also showing the modifier 24 arranged on the outer surface 23 of the resonator 16. The modifier 24 can consist of any substance or mixture of substances which will provide a binding site such that in the presence of a target molecule 25 a binding event will occur at the outer surface 23 of the resonator 16 inducing a perturbation in the light resonating within the resonator 16. For example, the modifier 24 as shown in FIG. 2a could be a functional group bound to the outer surface 23 of the resonator 16 such that a binding event occurs only in the presence of a specific target molecule or element 25. Alternatively, as shown in FIG. 2b, the modifier 24 could comprise a DNA strand bound to the outer surface 23 of the resonator 16 such that a binding event occurs only in the presence of a complimentary DNA strand 25.

Although the two figures only show modifiers 24 that are covalently bound to the outer surface 23 of the resonator 16, any suitable method of attaching the modifier 24 can be used, such as, covalent bonding or electrostatic bonding. Processes for modifying glass and silica substrates to allow specific agents to be bound to these surfaces are well known in the art. For example, a glass microsphere resonator 16 can be placed in a wash of selected pH to electrostatically charge the surface of the glass for later modification. Alternatively, the glass can be covalently modified by a covalent linker such as silylchloride, bovine serum albumin, or coated with an electrooptic material such as ZTO, etc. to provide an outer surface 23 to which a selected modifier 24 can then be covalently bound. Glass preprepared with an aldehyde containing reagent can be purchased from any number of suppliers, such as, for example, Telechem International, under the tradename SuperAldehyde Substrates. For small proteins or peptide binding, glass treated with bovine serum albumin and N,N'-disuccininmidyl carbonate has been used. In another embodiment, plastic microsphere resonators 16 are used which are pre-treated with a specific modifier 24 such as, for example, Biotin/Avidin which provide a suitable outer surface 23 for modification. Exemplary systems can be found in the following references each incorporated herein by reference: U.S. Pat. No. 5,143,854; U.S. Pat. No. 4,979,959; NATURE, vol. 352, pg. 445 (1991); SCIENCE, vol. 270, pg. 1653 (1995); and NATURE, vol. 387 [Mar. 15, 1997].

In addition, while only chemical functional groups and complimentary DNA strands are shown as modifiers 24 in FIGS. 2a and 2b, any suitable modifier 24 capable of undergoing a specific binding event could be used, such as, for example, antibodies to monitor for viruses or molecular machines, such as ribosome which takes in an RNA building block and builds DNA, to monitor for the presence of the RNA building block. Additionally, the modifier could be chosen such that some detectable change other than loss induced in the light resonating within the resonator 16 is detected, such as, for example, fluorescence from a fluorescent material coated on the outer surface 23 of the resonator 16.

In the embodiments shown in FIGS. 2a and 2b, the coupler 14 is a single fiber taper in proximal contact with a single modified resonator 16, however, it should be recognized that any arrangement of resonator 16 and coupler 14 can be employed. FIGS. 2c to 2g show several possible embodiments of the coupler/resonator pair 20. In the embodiment shown in FIG. 2c, the coupler 14 is a single fiber taper in proximal contact with the resonator 16, however, any other configuration which allows evanescent coupling of the light source 12 and the resonator 16 could also be used. For example, in FIG. 2d, a multiplicity of resonators 16 are coupled to a single taper waveguide coupler 14, in FIG. 2e a single resonator 16 is coupled to a dual-taper waveguide coupler 14, in FIG. 2f multiple resonators 16 are coupled to a dual-taper waveguide coupler 14, in FIG. 2g multiple resonators 16 are coupled to an array of waveguide couplers 14 arranged on a substrate 26. In FIG. 2g, each waveguide coupler 14 is supplied with a different wavelength of light $\lambda_1$ to $\lambda_5$ such that each resonator 16 can be monitored independently, however, any other arrangement of detection can be used such as different frequency or phases of light, or alternatively all the resonators 16 could be supplied with the same wavelength, frequency, etc. light and monitored by individual detectors 18. Additionally, while the pictured embodiment only shows microsphere resonators 16 coupled to waveguide couplers 14, any suitable combination and construction of at least one resonator or multiple resonators 16 with at least one coupler or multiple couplers 14 can be used so long as the coupler/resonator pair 20 is constructed so that light passing through the coupler 14 is evanescently coupled into the resonator 16.

Figure 2E:
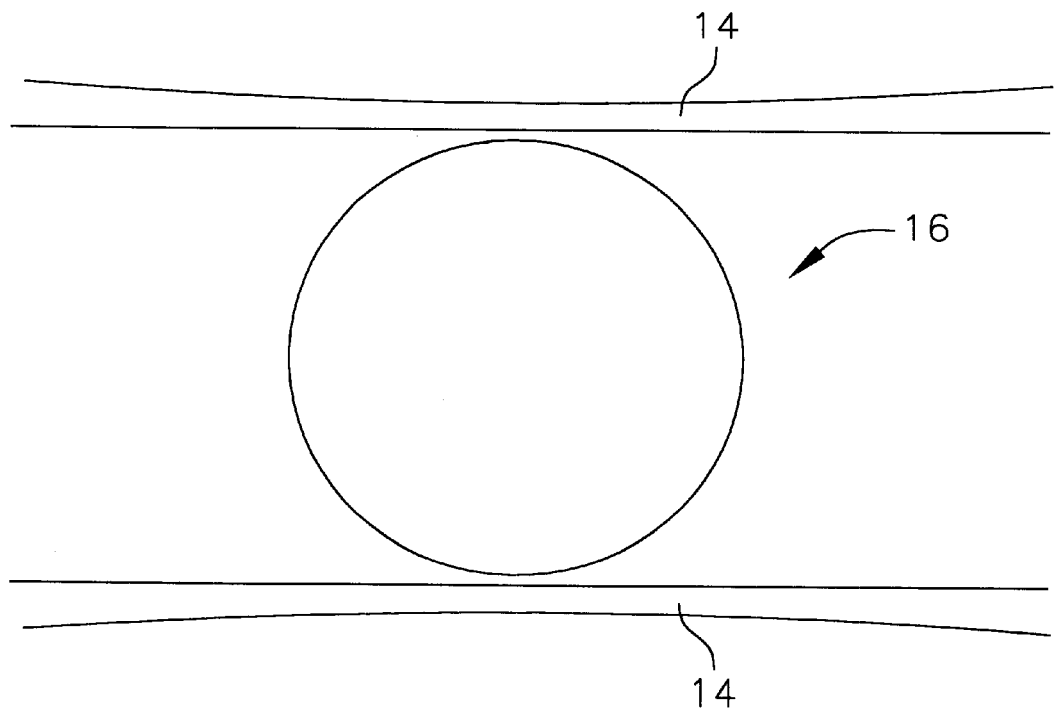
FIG. 2e is a schematic view of an alternative embodiment of the coupler/resonator scheme according to the invention.
Figure 2F:
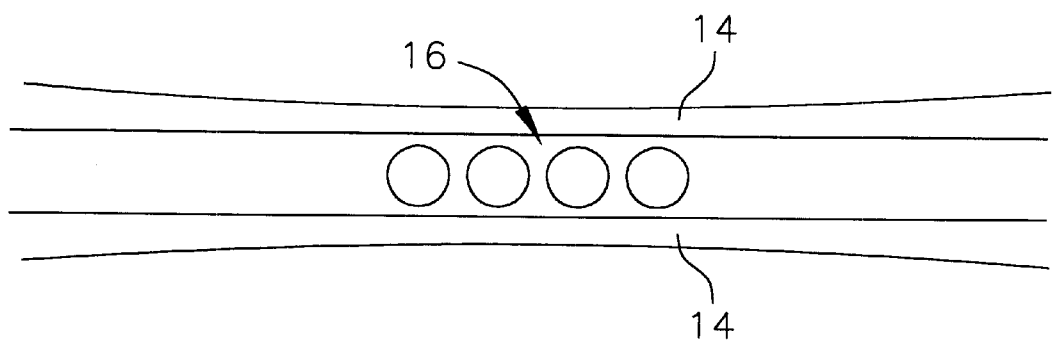
FIG. 2f is a schematic view of an alternative embodiment of the coupler/resonator scheme according to the invention.
Figure 2G:
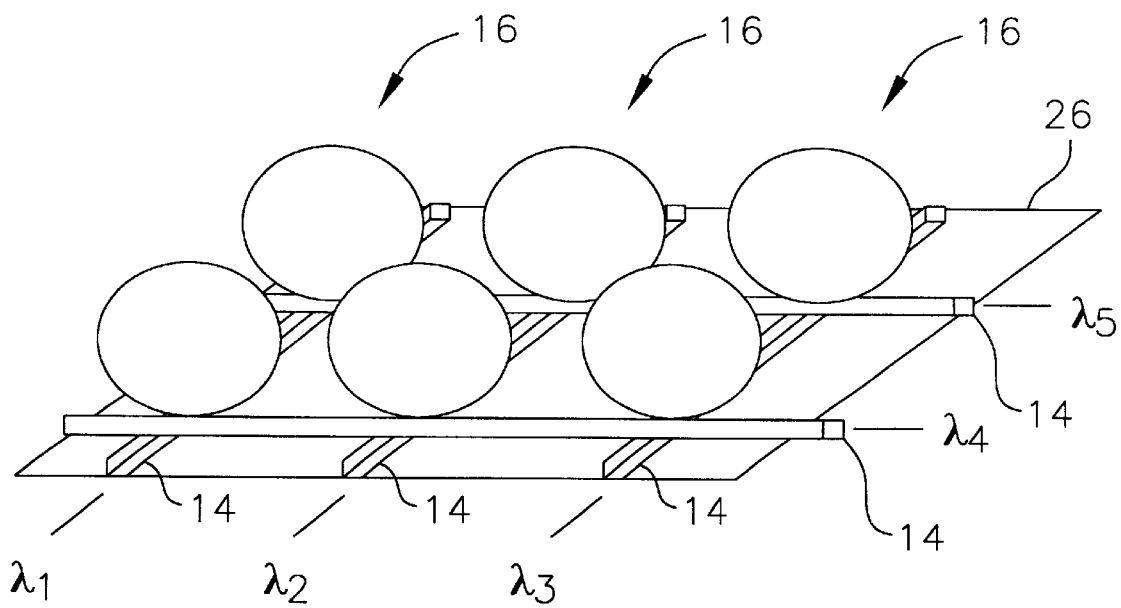
FIG. 2g is a schematic view of an alternative embodiment of the coupler/resonator scheme according to the invention.
Figure 3:
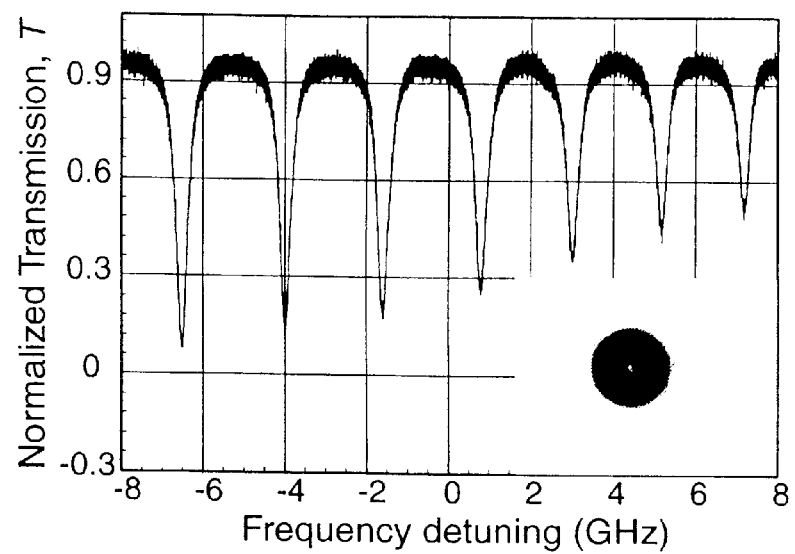
FIG. 3 is a graphical representation of the of the signal response properties of the present invention.

A prototype of the dual-taper microsphere resonating sensor 10 described above was constructed utilizing a dual-taper waveguide 14 having diameters in the range of 3 to 5 microns prepared from standard telecommunication fiber and a silica microsphere resonator 16 having a diameter ranging from 50 to 150 microns prepared by a $CO_2$ laser as described and shown in FIG. 2e above and shown in the inset to FIG. 3. To ensure evanescent coupling, the fiber taper waveguides 14 were placed in physical contact with opposite ends of the microsphere resonator 16. A single-frequency tunable laser was used as a source of light 12 and was placed in optical communication with the proximal end of the fiber taper waveguide 14. The tunable external-cavity diode laser with a linewidth of less than 300 kHz was scanned over a 15 GHz range. A optical spectrum analyzer detector 18 was placed in optical communication with the distal end of the fiber taper waveguide to measure the transmission spectrum of the resonating sensor system 10. FIG. 3 shows the results of a typical transmission spectrum for the microsphere-taper detector system with no induced loss. In a transmission measurement the optical frequency of the input wave is swept over some range of values while monitoring the transmitted optical power. As the frequency of the input beam comes into resonance with the frequency of a WGM resonance, the optical power is observed to decrease as illustrated in FIG. 3. The spectral width of the measured power transmission minimum is given by the ratio of the WGM line center frequency to the Q of the mode as follows:

$$Q = \frac{v_o}{\Delta v}$$

where $\Delta v$=half width at half maximum. The amount of light coupled from the light source 10 through the dual-taper waveguide coupler 14 to the whispering-gallery modes of the microsphere resonator 16 are shown as a drop in the amount of light transmitted through the waveguide 14 to the detector 18. As shown in FIG. 3, coupling efficiencies as high as 99% were routinely observed utilizing the dual-taper silica microsphere sensor system.

Figure 4:
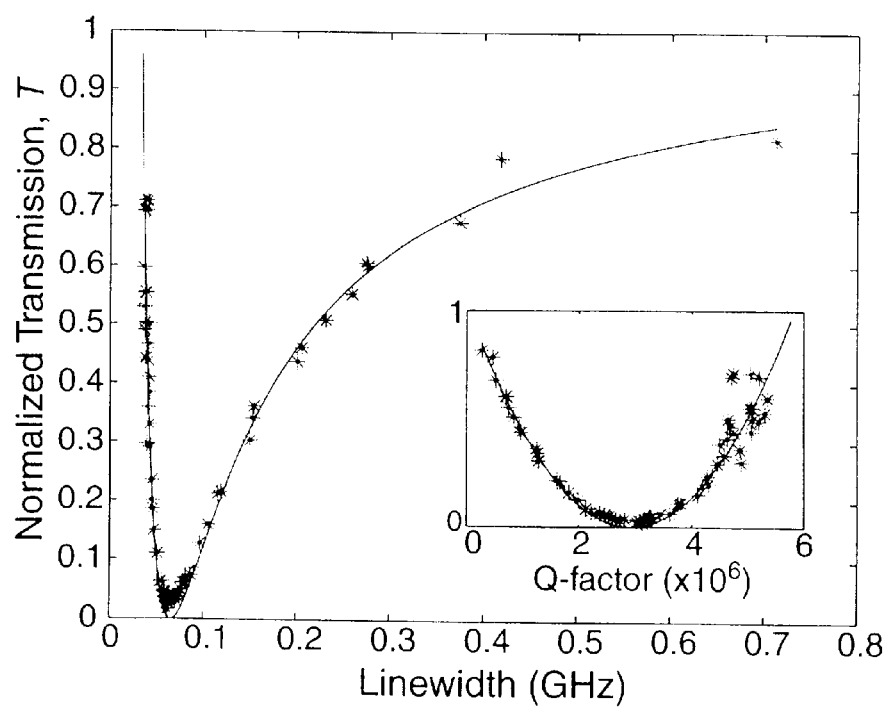
FIG. 4 is a graphical representation of the signal response properties of the present invention.

In this exemplary embodiment, loss was induced in the resonating system by bringing a loss probe in proximity to the microsphere resonator 16. By approaching the probe to the surface of the resonator 16, the total cavity loss of the resonant modes was increased due to the probe scattering and absorption. The loss induced by the probe is intended to model the loss that would be induced by a binding event between a modifier 24 and a binding agent. The loss probe was constructed with a plastic tip having a diameter comparable to the microsphere diameter so as to minimize probe-induced backscattering within the resonator 16. The loss probe was made of a plastic material that absorbs in the 15 GHz band so that power coupled from the resonator 16 would be quickly absorbed by the loss probe. A piezoelectric motor variably positioned the probe near the resonator 16 with a 0.2 $\mu$m resolution. FIG. 4 shows the result of tests of transmission response to induced loss. In this plot, the on-resonance power transmission is shown plotted versus the linewidth of the resonant whispering-gallery mode. Linewidth is a convenient measure of the mode loss and increase as the probe position is advanced towards the sphere.

As shown in FIG. 4, prior to the probe being brought into close proximity of the microsphere, the taper-microsphere system is biased well into the overcoupling regime (T<70%). In fact overcoupled transmissions of greater than 99% have been observed for this system indicating that most of the light energy transmitted to the detector 18 comes from light that has been coupled to the whispering-gallery modes of the resonator 16 and then exits the resonator 16 back into the waveguide 14 after a number of light cycles as determined by the Q-factor of the resonator 16. As the probe is brought nearer the resonator 16 some portion of the light resonating within the resonator 16 is lost as a result of the probe's presence such that the amount of light reentering the coupler 14 from the resonator 16 decreases. This is alternatively illustrated in the inset to FIG. 4, which shows depicts a plot of the Q-factor verse transmission. As shown in both plots, as the probe is brought into close proximity with the resonator 16 a clear minimum versus probe position is apparent in the figure, corresponding to the critical point. At this point the quantitative loss of light energy from the resonator 16 nearly equals the quantity of light energy coupled into the resonator 16 from the coupler 14 such that all of the light coupled into the resonator 16 escapes through the loss probe so that only the 1% of light energy not coupled into the resonator 16 reaches the detector 18. Moving the probe in even closer to the resonator 16, past the critical point, leads to a decrease in coupling efficiency such that more light passes through the waveguide 14 directly to the detector 18 bypassing the resonator 16. In this undercoupled regime, eventually the resonator system coupling efficiency is decreased to a point such that no coupling occurs, and nearly all of the light from the light source 12 passes directly through the waveguide 14 to the detector 18 thus increasing the amount of light transmitted to the detector 18.

Although these graphs show a transmission spectrum, it should be noted that any suitable spectrum could be taken. For example, a modifier 24 could be bound to the resonator 16 which induces an initial loss in the resonator 16 absent a binding event such that only a small fraction of the light coupled to the modified resonator 16 reaches the detector (i.e., a resonator that operates prior to binding with the binding agent at the critical point of the graph shown in FIG. 4). Interaction with the substance of interest would then increase the transmission of light to the detector, either as the loss decreased, leading to overcoupling, or as the loss increased, leading to undercoupling.

Figure 5:
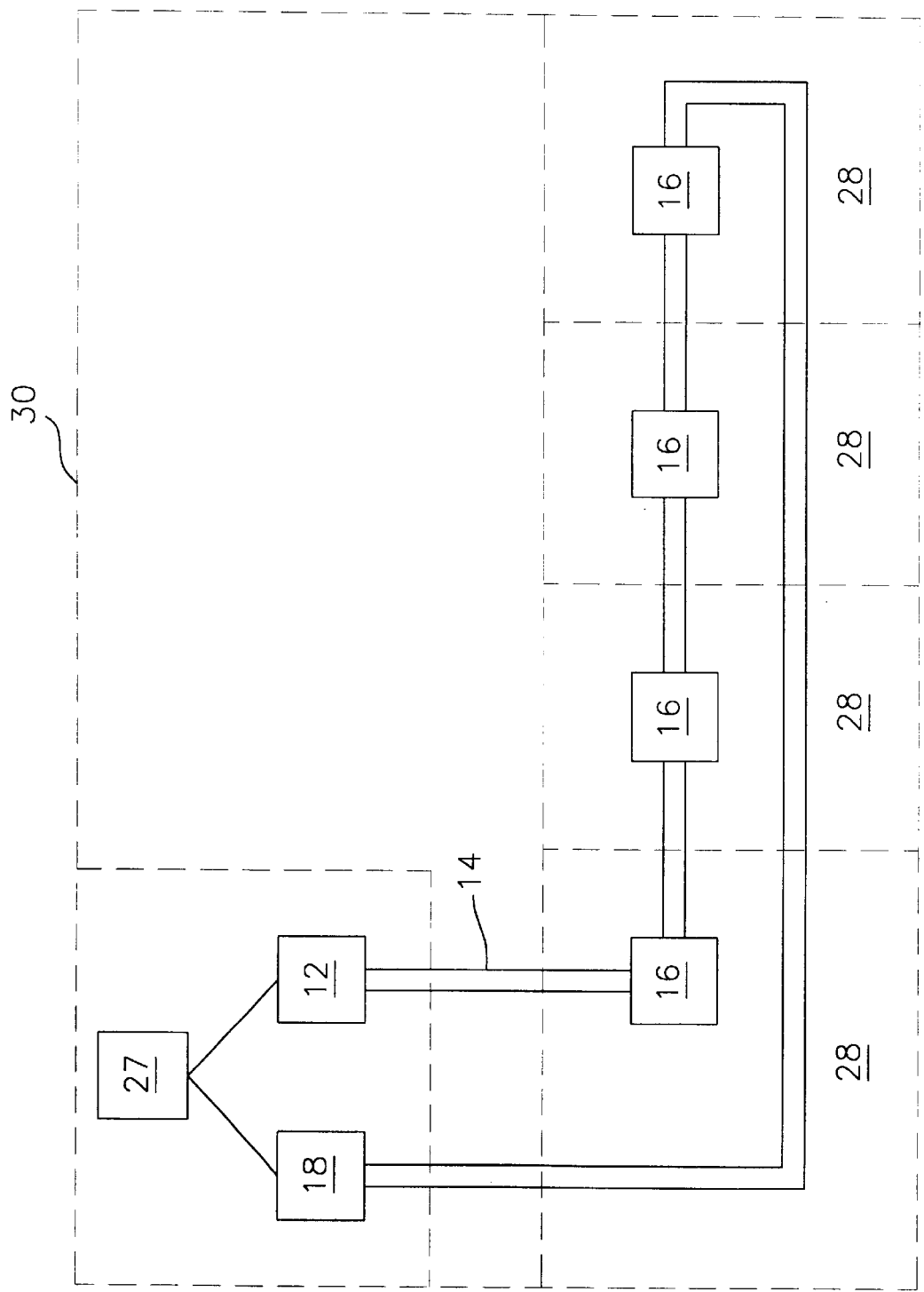
FIG. 5 is a schematic representation of an embodiment of a system utilizing the sensor according to the invention.
Figure 3:
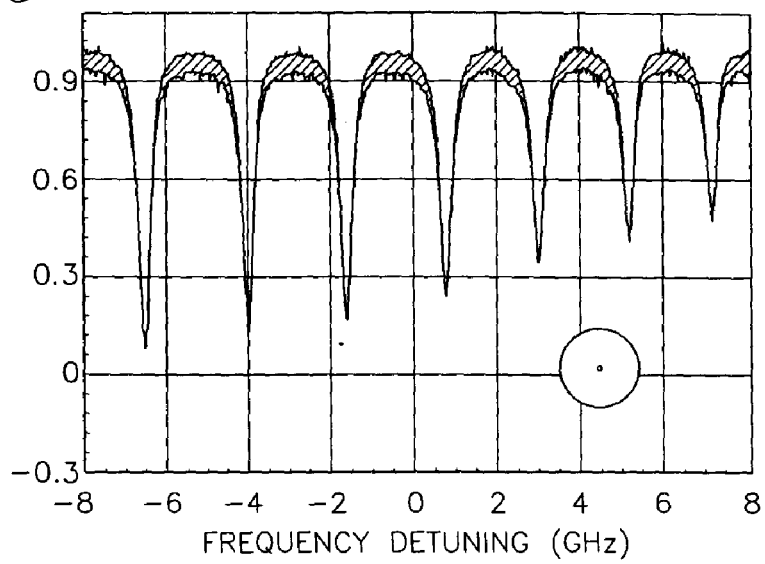
Figure 4:
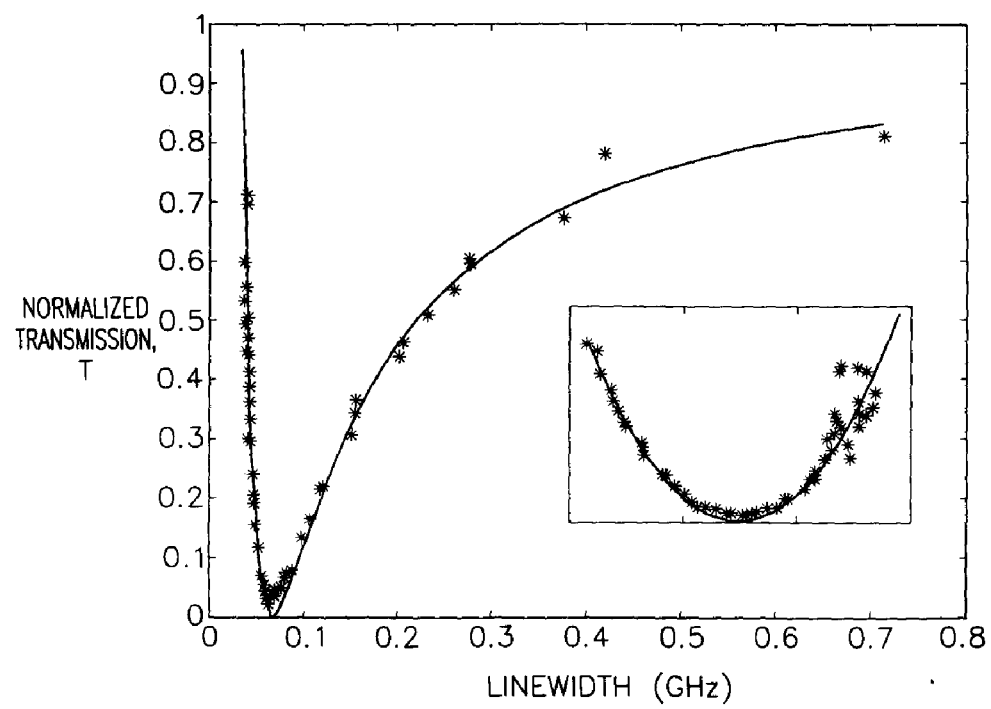

Although this specific embodiment shows a single coupler/resonator 20 having a single modifier species 24 it should be understood that the present invention also encompasses a system of sensors either singly or multiply directed to detecting and discriminating a substance or multiple substances of interest. FIG. 5 shows an embodiment of the system comprising a single source of light 12, in optical communication with a taper-fiber waveguide coupler 14, which itself is evanescently coupled to a series of resonators 16 along its length and a detector 18 at its distal end. The detector 18 and the light source 12 are data linked via a central terminal 27 such that activation and monitoring of the sensors can be synchronized and recorded. As shown in FIG. 5, the resonators are positioned at detection points in separate rooms 28 throughout a multi-roomed building 30, such that a user at the central terminal 27 can monitor for substances of interest throughout the building 30 simultaneously. Differentiation of the signals from the various resonators 16 can be accomplished by having a tuneable light source 12 and by having each resonator 16 respond to a different wavelength or frequency of light from the light source 12 such that by having the source of light 12 constantly scan over a range of wavelengths or frequencies any number of resonators 16 could be monitored. The central terminal 27 would then synchronize the light source 12 and the detector 18 such that the detected wavelength and the scanned wavelength would correspond at any given moment in time. Alternatively, a separate light source 12, a separate coupler 14, or a separate detector 18 could be used for each resonator 16 such that each resonator 16 was monitored continuously. In this embodiment, the central terminal 27 would be supplied with a series of input channels such that the signals from each source/coupler/resonator/detector could be monitored and recorded simultaneously. Although only a single resonator is positioned per room 28 in the embodiment shown in FIG. 5, any number of resonators 16 and or waveguides 14 could be run into a single room 28. Furthermore, while each resonator 16 might be modified to detect a single substance, the resonators 16 might also be individually modified to detect different substances.

Although specific embodiments are disclosed herein, it is expected that persons skilled in the art can and will design alternative resonator sensor systems that are within the scope of the following claims either literally or under the Doctrine of Equivalents.

What is claimed is:

1. A resonant sensor for detecting the presence of a substance, said sensor comprising:
   a source of light;
   at least one coupler adapted to receive light from the source of light and conduct it therealong;
   at least one resonator each of said at least one resonators having at least one high Q-factor resonant mode therein, said at least one resonator coupled to the at least one coupler to store a specified amount of light energy therefrom in the at least one high Q-factor resonant mode for a specified period of time based on the Q-factor of said at least one high Q-factor resonant mode and then release a specified amount of said light from said at least one resonator, said at least one resonator having an outer surface; and
   a modifier deposited on said outer surface, said modifier adapted to interact with an at least one substance of interest such that during said interaction the proximity of the substance of interest to the at least one resonator alters the Q-factor of the at least one high Q-factor resonant mode of the at least one resonator such that the specified amount of light capable of being coupled into the at least one high Q-factor resonant mode of the at least one resonator is altered; and
   a detector adapted to detect the alteration of the light released from said at least one resonator and produce an output signal.

2. A sensor as described in claim 1, wherein the at least one resonator is evanescently coupled to the coupler.

3. A sensor as described in claim 1, wherein the at least one high Q-factor resonant mode is a whispering-gallery mode.

4. A sensor as described in claim 1, wherein the at least one resonator is a microsphere.

5. A sensor as described in claim 4, wherein said microsphere is made of fused silica.

6. A sensor as described in claim 1, wherein the at least one coupler is selected from the group consisting of a fiber taper waveguide, a D-fiber waveguide, a ridge waveguide, a slab waveguide and a prism.

7. A sensor as described in claim 1, wherein the detector monitors the lasing spectrum of light as modified by the at least one high Q-factor resonant mode of the at least one resonator.

8. A sensor as described in claim 1, wherein the detector monitors the reflection spectrum of light as modified by the high Q-factor resonant mode of the at least one resonator.

9. A sensor as described in claim 1, wherein the detector monitors the transmission spectrum of light as modified by the high Q-factor resonant mode of the at least one resonator.

10. A sensor as described in claim 1, wherein the detector monitors the fluorescence of light as modified by the high Q-factor resonant mode of the at least one resonator.

11. A sensor as described in claim 1, wherein the modifier is adapted to adjust the refractive index of the resonator in the presence of the substance of interest.

12. A sensor as described in claim 1, wherein the modifier comprises a chemically active agent.

13. A sensor as described in claim 1, wherein the modifier comprises a biologically active agent.

14. A sensor as described in claim 1, comprising a single one of the at least one waveguide evanescently coupled to a single one of the at least one resonator.

15. A sensor as described in claim 1, wherein at least two of the at least one coupler are evanescently coupled to a single one of the at least one resonator.

16. A sensor as described in claim 1, comprising a single coupler evanescently coupled to more than one resonator.

17. A sensor as described in claim 1, comprising at least two of the at least one coupler each independently evanescently coupled to a separate one of the at least one resonator.

18. A sensor as described in claim 1, wherein the light source is a variable wavelength light source.

19. A method for detecting the presence of a substance, comprising the steps of:
   providing at least one sensor as described in claim 1;
   exposing the at least one sensor to a sample;
   monitoring the output signal of the detector to determine the presence of at least one species of interest.

20. A system for detecting the presence of a substance, comprising at least one sensor as described in claim 1, wherein the output of the detector is in data communication with a central terminal adapted to monitor and record the output signal and communicate said output signal to a user.

* * * * *

UNITED STATES PATENT AND TRADEMARK OFFICE
CERTIFICATE OF CORRECTION

PATENT NO. : 6,583,399 B1
DATED : June 24, 2003
INVENTOR(S) : Hunziker et al.

It is certified that error appears in the above-identified patent and that said Letters Patent is hereby corrected as shown below:

Title page,
Item [56], References Cited, OTHER PUBLICATIONS, delete
"Gorodetsky, et al., High-Qoptical", insert -- Gorodetsky, et al., High-Q optical --

Drawings,
Delete Drawing Sheet 6 and substitute therefor the Drawing Sheet, consisting of Figs. 3 and 4, as shown on the attached page.

Column 10,
Lines 21-23, delete "one coupler is selected from the group consisting of a fiber taper waveguide, a D-fiber waveguide, a ridge waveguide, a slab waveguide and a prism", insert -- one coupler is any of a fiber taper waveguide, D-fiber waveguide or prism --
Lines 50-51, delete "comprising a single coupler evanescently coupled to more than one resonator", insert -- comprising a single one of the at least one coupler evanscently coupled to at least two of the at least one resonator --

Signed and Sealed this

Twenty-eighth Day of June, 2005

JON W. DUDAS
*Director of the United States Patent and Trademark Office*